United States Patent [19]

Herpichböhm

[11] Patent Number: 4,852,025
[45] Date of Patent: Jul. 25, 1989

[54] SYSTEM FOR DETERMINING THE CONCENTRATION OF COMPONENTS OF BODY FLUIDS

[75] Inventor: Bernd Herpichböhm, Mannheim, Fed. Rep. of Germany

[73] Assignee: Boehringer Mannheim GmbH, Mannheim, Fed. Rep. of Germany

[21] Appl. No.: 13,396

[22] Filed: Feb. 11, 1987

[30] Foreign Application Priority Data

May 22, 1986 [DE] Fed. Rep. of Germany ....... 3617161

[51] Int. Cl.[4] ............... G06F 15/42; G01N 33/16
[52] U.S. Cl. ................ 364/551.01; 364/497; 364/413.08; 364/413.11; 356/39; 128/633
[58] Field of Search ............ 364/413, 415–417, 364/497–499, 550, 551, 555, 551.01, 413.18, 413.22, 413.07–413.09, 413.11; 128/632, 633, 637; 356/39, 436

[56] References Cited

U.S. PATENT DOCUMENTS

| | | | |
|---|---|---|---|
| 4,125,828 | 11/1978 | Resnick et al. | 364/416 |
| 4,128,884 | 12/1978 | England | 364/416 |
| 4,281,387 | 7/1981 | Kraft et al. | 364/497 |
| 4,420,564 | 12/1983 | Tsuji et al. | 364/415 |
| 4,472,505 | 9/1984 | Manabe et al. | 364/498 |
| 4,612,614 | 9/1986 | Deindoerfer et al. | 364/415 |
| 4,642,778 | 2/1987 | Hieftje et al. | 364/498 |
| 4,685,059 | 8/1987 | Yamamoto | 364/415 |
| 4,706,207 | 11/1987 | Hennessy et al. | 364/416 |
| 4,720,788 | 1/1988 | Golias | 364/416 |

Primary Examiner—Parshotam S. Lall
Assistant Examiner—Brian M. Mattson
Attorney, Agent, or Firm—Felfe & Lynch

[57] ABSTRACT

The disclosed system determines the concentration of components of body fluids using test carriers and an instrument to evaluate the test carriers. The instrument has an electronic evaluating system with a processor which, on the basis of information transmitted to it concerning the batch-specific evaluation curve of the particular test carrier batch used, calculates the concentration (C) from a value (R) measured on the test carrier. The information about the evaluation curve is contained in visible indicia printed on each test carrier itself or on material for packaging, or packaged with, multiple test carriers.

25 Claims, 5 Drawing Sheets

# SYSTEM FOR DETERMINING THE CONCENTRATION OF COMPONENTS OF BODY FLUIDS

BACKGROUND OF THE INVENTION

The present invention relates to a system (method and apparatus) for determining the concentration of certain constituents of a body fluid, such as urine or blood.

Recently, test carriers, for example in the form of test strips or in the form of flat, approximately square platelets, have been used increasingly for the analysis of body fluids, especially of urine and blood. Analytical determinations, especially for medical purposes, can be carried out particularly easily with these test carriers. The test carriers are first of all brought into contact with the sample. When examining urine, this is generally done by dipping a strip-shaped test carrier into the urine. For examining blood, a drop of blood is usually applied on the test field of the test carrier and, after saturating the test field, is wiped or washed off. In each case, the test field, which represents the part of the test carrier that is crucial for the analytical determination, contains reagents that react with the components of the body fluid that has been applied.

To evaluate the reaction, the test carrier is placed in appropriate evaluating equipment, in which a physical quantity, which serves as a measure of the concentration of a particular component of the body fluid, is measured at a specified time after the sample is applied. To analyze body fluids, a reaction is predominantly used that produces a color change characteristic of the analysis to be carried out. In this case, the diffuse reflectance of the test field at a particular wavelength is usually determined as the physical quantity measured. Such test carriers can thus be evaluated photometrically. In a different, known type of test carrier an electrochemical reaction is utilized to analyze the body fluid. In this case, a voltage or an amperage is determined as the physical quantity characteristic of the analysis.

The test carriers are usually suitable specifically for a particular analysis: that is, for determining the concentration of a specific component of a body fluid - a so-called "parameter". Thus, for each parameter it is necessary to provide a particular test carrier type. To evaluate the test carriers, equipment is used which is either adapted specifically to one such carrier type (single parameter equipment), or which can measure several different test carriers (multiparameter equipment).

The test carrier and the associated evaluating equipment, which together form a system, must satisfy very high accuracy requirements. Usually, a large number of test carriers is produced together under constant conditions. For example, for photometrically evaluable tests, a particular carrier matrix for the test fields and a single preparation of reagents is used for one manufacturing batch. The test carriers of such a manufacturing batch are therefore practically identical in their properties. On the other hand, test carriers from different manufacturing batches deviate from one another with respect to their evaluation curves; for example, in the relationship between the diffuse reflectance of the test field and the concentration of the sought-after parameter which is to be determined by the equipment. These deviations are so large, that the high requirements set in medicine for quantitative determinations cannot be fulfilled if the differences between the different manufacturing batches are disregarded.

In principle, the desired accuracy could be attained by calibrating with standard solutions before each use of the test carrier. This, however, makes it more difficult and time consuming to utilize the analytical system.

It has therefore already been previously proposed to transmit, in a suitable manner, that information concerning the batch -specific evaluation curve of the respective test carrier batch to the evaluating equipment. For example, as is described in U.S. Pat. No. 4,592,893, the individual test carriers may be provided with a bar code, which contains information relating to the batch-specific evaluation curve. The associated evaluating equipment contains a bar-code reader to pick up this information. U.S. Pat. No. 4,578,716 describes strip-shaped test carriers which have a magnetic layer that is also suitable for the storage and retrieval of information. This information is written into the magnetic layer by the manufacturer of the test carrier and sensed by the evaluating equipment with an appropriate magnetic read head.

These two known transmitting techniques are particularly convenient to handle because the necessary information is in each case communicated automatically to the equipment without any intervention whatsoever by the user. This advantage is, however, accompanied by considerable cost. In manufacturing the test carrier, the information must be transferred to each individual test carrier and special test carriers, coordinated with the respective instrument type, must be produced. In the evaluating instrument, there must be an appropriate reading device which increases the cost of the instrument appreciably.

For simpler equipment, especially for determining blood glucose values for diabetics, it is therefore largely customary to disregard the batch-specific variations of the test carriers. This, however, leads to medically intolerable inaccuracies.

In a different, known instrument for determining blood glucose, the batch-specific evaluation curve, in the form of a bar code, is included separately from the test carriers in the test-carrier packages. The costs of manufacturing the test carrier are thus reduced. However, in this case, the equipment must also have a code reader and thus becomes appreciably more expensive.

SUMMARY OF THE INVENTION

It is an object of the present invention to improve an evaluating system of the initially described type in such a process that the batch -specific evaluation curve is taken into consideration, so that an accuracy fully satisfying medical requirements is reached while, at the same time, the manufacturing costs of the test carriers as well as of the evaluating equipment are as advantageous as possible.

This object, as well as other objects which will become apparent in the discussion that follows, are achieved, according to the present invention, by providing a test carrier for use in a system for determining the concentration of a constituent of a body fluid, with which is associated a number of visible indicia, each representing a different calculation supporting point in the vicinity of the ends, and the points of inflection of a standard, predictable, nonlinear curve, these calculation supporting points being indicative of the actual dependency between the physical quantity to be measured and the concentration to be determined in the vicinity of such ends and points of inflection.

More particularly, the visible indicia associated with a test carrier may each identify a particular calculation supporting point from among a stored set of prescribed calculation supporting points.

A "calculating supporting point", as used herein, is intended to mean an associated coordinate value pair of a measured physical quantity (R) and a constituent concentration (C) in an R-C coordinate plane. Each set of calculating supporting points is located, respectively, in the vicinity of one of the ends or one of the points of inflection of the aforementioned standard curve on the R-C plane. The particular calculating supporting points identified by the indicia are those closest to the actual dependency between the measurable physical quantity and the concentration for the particular test carrier in question.

The visible indicia, which are preferably alphanumeric characters, may be printed on the test carrier itself. Preferably, however, the visible indicia are imprinted on the package containing a number of test carriers which are manufactured together in a single batch. Alternatively, the indicia may be printed on a separate, removable instruction sheet wrapped in a common package with the test carriers of a single batch.

On the basis of the invention, the evaluating instrument can very easily be adjusted to evaluate the respective test strip batch. If, for example, a sequence of numbers or characters is printed on the package for the test carrier, the number of characters may correspond to the number of sets of calculation supporting points. This sequence may be manually set on the instrument by means of a suitable input device. For example, decade switches, with a number of places that correspond to the number of sets of calculation supporting points and which can be set in each case, for example, to 10 different values, may be used. A different possibility is to provide appropriate keys which can be used to enter the code as will be described in greater detail below. In each case, the user of the instrument must check the code of the batch only once when starting a new package of test carriers and, if desired, may appropriately change the setting of the input device of the instrument. On the basis of these few inputs, the instrument, by means of its microprocessor, calculates the concentration from the physical quantities measured, thus determining these concentrations with an accuracy which previously was impossible with such simple equipment.

This achievement of the objects of the present invention is based essentially on the recognition that, within the scope of the present invention, the different evaluation curves of different test carrier batches can be reconstructed with very good accuracy from a single standard curve if the standard curve is given a shape similar to that of the batch-specific evaluation curves and if calculation supporting points are defined in the vicinity of the points of inflection as well as of the ends of the standard curve. This will be explained in greater detail below with the aid of the drawings.

The fact that the inventive evaluating instrument does not require a code reader not only lowers its cost of manufacture, but also permits a particularly compact construction. This is of importance also medically because especially diabetics should measure their blood sugar level under living conditions which are as normal as possible and should, therefore, use the measuring instrument also away from home. The acceptance and use of a system for determining blood sugar is naturally increased if the instrument is smaller and more easily transportable.

Generally speaking, the invention permits a considerable reduction in the amount of information which must be transmitted in order to exactly define the batch-specific evaluation of test carriers. Not only is the transfer of the evaluation curve to the instrument simplified in this manner, but so also is the processing of the information in the instrument itself. Consequently, a simpler 4-bit microprocessor can frequently be used instead of an appreciably more expensive 8-bit microprocessor. This also results in a considerable savings in cost and in construction size.

The invention is explained in greater detail hereinbelow by means of an embodiment of the system shown in the drawings.

DESCRIPTION OF THE PREFERRED EMBODIMENTS

Figure 1:
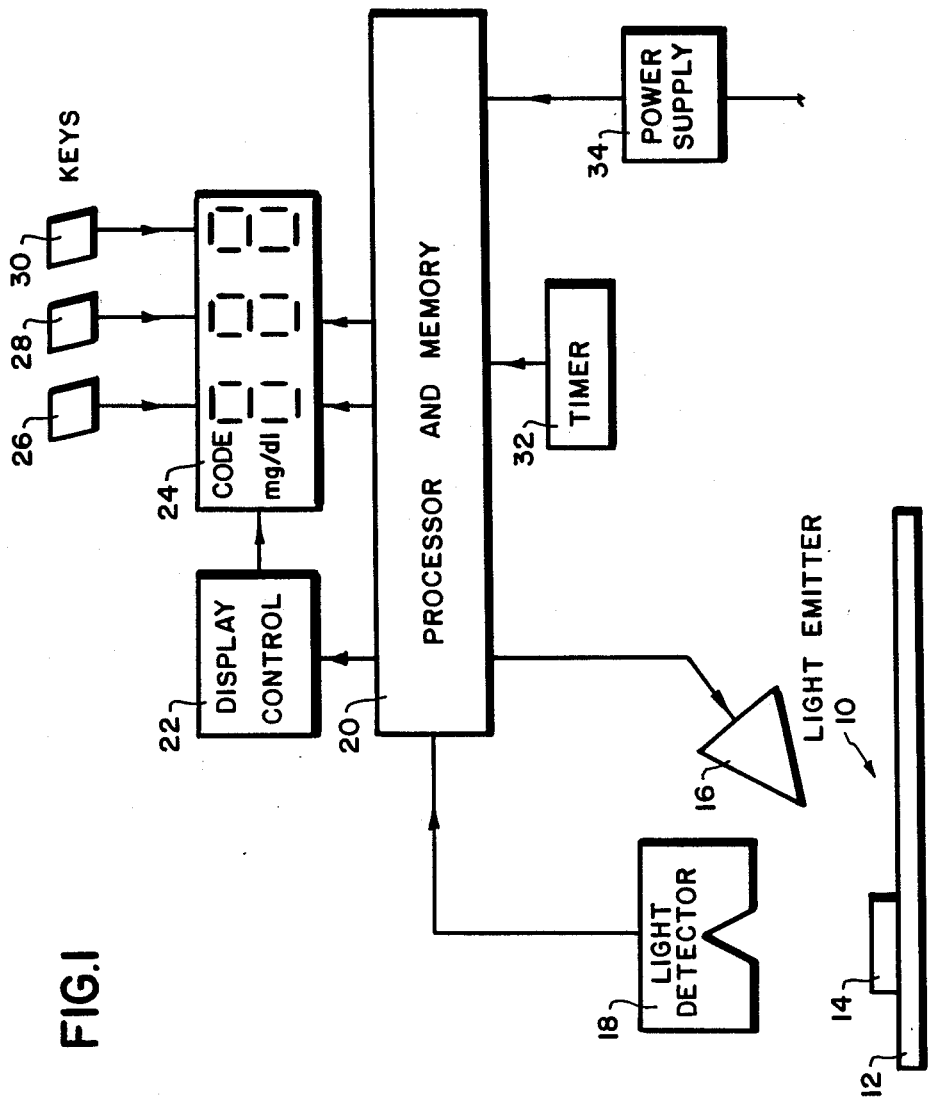
FIG. 1 is a block circuit diagram of an evaluating instrument for test carriers according to the invention.

FIG. 1 illustrates those components of an evaluation instrument for test carriers which are essential for understanding the present invention. A test carrier 10, comprising a base 12 and an attached test field 14, is seen in the lower left-hand corner. The test field is impregnated with reagents which, when contacted by a body fluid sample, produce a color change characteristic of the sought-after parameter. The test carrier is represented in FIG. 1 in a simplified form. The test carriers of today frequently have a quite sophisticated construction in order to make very accurate measurements possible.

The test field is illuminated by the light produced by a light emitter 16. This light, diffusely reflected from the surface of the test field 14, is detected by a sensing device 18. The sensing device usually comprises a light-sensitive detector; for example, a photodiode, an amplifier and an analog-digital converter. Suitable sensing devices are well known in the art.

The central element of the instrument is a processor with an associated memory which form a microcomputer 20. This computer serves to control the different instrument functions and to convert the physical quantities supplied by the sensing device 18 into the desired concentration values. The values, so calculated, are shown by means of a display control system 22 on a display device 24. A digital display is usually used as the display device.

In order to be able to calculate the corresponding concentration values from the physical values measured, the computer 20 requires information concerning the actual batch-specific evaluation curve. In the inventive embodiment shown, this information is entered by means of three keys 26, 28, 30. The values, selected with the aid of these keys, are shown on the display device 24. When the values indicated on the display device 24 correctly reproduce the code (as set forth, for example, on the test carrier or test carrier package), the computer 20 is given the command to accept and store this code.

The display may be formed, for example, as a conventional 7-segment display which is capable of representing the ten numbers of the decimal system as well as a series of alpha characters. In a preferred, practical embodiment, each of the positions of the display can show 16 different alphanumeric characters so that, for each position of the code, 16 different discrete values can be selected with the aid of the keys 26, 28 and 30 and transmitted to the computer 20. The number 16 is particularly preferred because up to 16 different values can easily be coded and processed by means of a 4-bit word within the computer. However, depending upon the requirements of the system, a different number of discrete setting values may also be used.

Furthermore, a timer 32 for controlling the microprocessor and a power supply 34 for the system can be seen in FIG. 1. Other conventional elements, such as devices for controlling the operating voltage and the like, are not shown for the sake of clarity.

The invention thus relates to a method for calculating the concentration of a constituent of a body fluid from a measured physical quantity, such as the diffuse reflectance to a particular wavelength of light. This method is carried out with the aid of a code, which consists of only a few digits or letters having, in each case, only a small number of discrete values, which are entered via keys 26, 28, 30 and a display device 24. This method of calculation will now be described in greater detail with reference to FIGS. 2 and 3.

Figure 2:
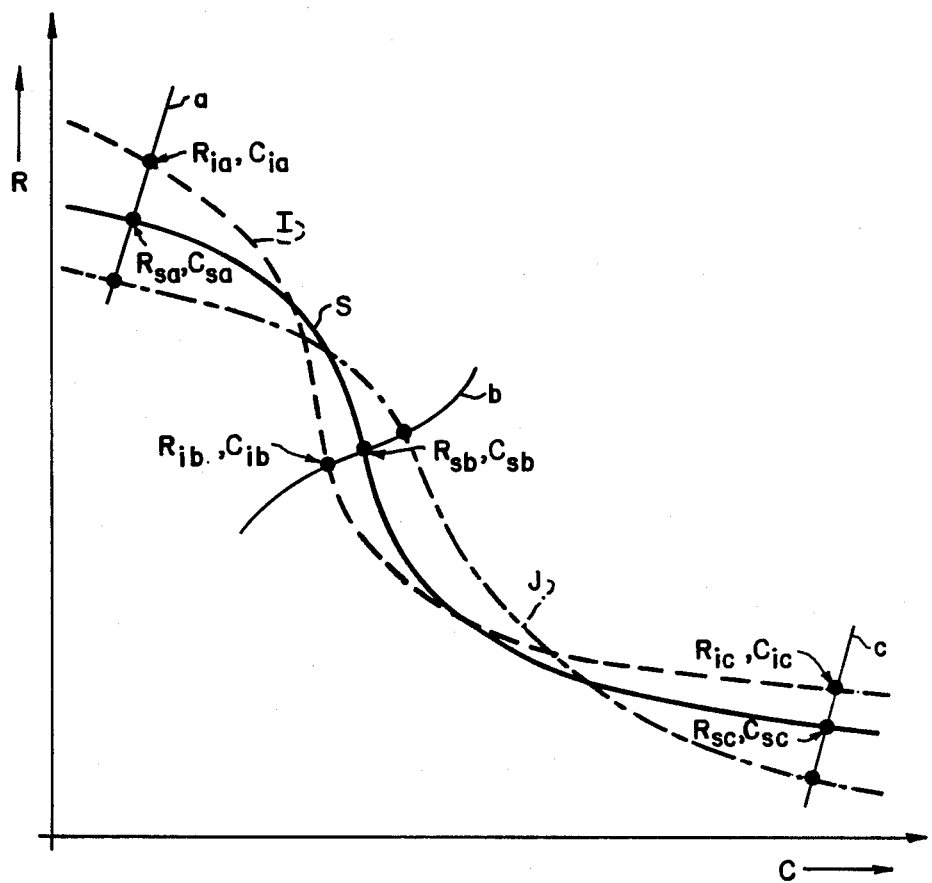
FIG. 2 is a graphic representation of two batch-specific evaluation curves and a standard evaluation curve.

Three curves, S, I and J are shown in FIG. 2. The broken curve I represents an exemplary characteristic of an evaluation curve for an optical test to determine the glucose level in blood. The diffuse reflectance R at a particular measuring wavelength determined by the optical system of the instrument is plotted on the ordinate. The corresponding concentration of the parameter to be determined, in this case glucose, is plotted on the abscissa. It can be seen from curve I that, because of the characteristic properties of the test fields of the analytical test carrier, the diffuse reflectance R at low concentration values is high. In the middle range of the concentration, it decreases increasingly with a convex curvature as viewed from the upper right corner of the figure. The curve then passes through a point of inflection into a concave curvature. The diffuse reflectance R falls less steeply with increasing concentration C in this region and finally, at high concentrations, changes only a little.

The general characteristic of the evaluation curves of test carriers depends upon the reagents chosen and on other properties of the test carriers and, therefore, is different from test type to test type. A curve of the type shown here is, however, typical for many cases. It has the advantage that, in the middle of the range, the slope of the curve, showing reflectance as a function of concentration, is steep. This is advantageous for a high measuring accuracy.

As has been mentioned, the evaluation curves for different test carriers of different manufacturing batches are not the same. For example, a different evaluation curve, labelled J, is drawn as a dot-dash line in FIG. 2. It can be seen that this curve is considerably different from evaluation curve I. However, it is identical with this curve in some basic properties. In particular, it also initially has a convex and, then after a point of inflection, a concave course as seen from the upper right. It should, however, be emphasized that each test carrier batch has a different evaluation curve so that there is an infinitely large number of possible evaluation curves which can be taken into consideration in good approximation within the scope of the invention.

It is essential for the present invention that a standard evaluation curve be fixed and stored in the memory of the evaluating instrument computer and that the characteristic of this standard curve be similar to that of the actual evaluation curves in the sense defined hereinbelow. Such a standard evaluation curve is drawn as a solid line in FIG. 2, where it is labelled S.

The standard evaluation curve should, first of all, cover the range of values of the actual evaluation curves. This means that the standard evaluation curve lies at least in the desired concentration range within the extreme values of the physically measured quantities of the evaluation curves of the test carriers occurring in practice. As shown in FIG. 2, these extreme values are not marked constantly by the same evaluation curves. In the embodiment shown, curve I, for example, has particularly high R values in the regions of low and high concentrations and curve J particularly low R values. In the middle of the concentration range, the situation is the reverse. The standard calibration curve S should lie somewhere in the region of the actual evaluation curves. In many cases, it is particularly advantageous if the standard calibration curve lies in the middle of the range of values of the actual evaluation curves; that is, approximately in the center of the actual evaluation curves of different test carrier batches obtained by a large number of preliminary experiments.

Moreover, the standard evaluation curve should have a convex and a concave curvature essentially or substantially in the same segments of values of the diffuse reflectance as the actual evaluation curves. Quantitatively, it may be stated that the points of inflection between the convexly and concavely curved regions of the standard curve should be at values of the diffuse reflectance R, that the values of the diffuse reflectance, corresponding to the points of inflection of the possible actual evaluation curves of the test carrier batches, differ by no more than 20%, and preferably by no more than 10%, from these standard values.

As can be seen from FIG. 2, the concentration ranges, in which curves I and J have the same curvature, do not agree very well. More particularly, the point of inflection does not occur at the same concentration value. It is, therefore, not possible and also not necessary that the standard evaluation curve have the same curvature in exactly the same segments of concentration values as the actual evaluation curves. It is sufficient if these substantially coincide so that adequately accurate values of the measurement results are attained by the iteration procedure described in detail below.

The standard curve may be expressed, for example, in the form of a polynomial, the coefficients of which are stored. Preferably, it is described as a polygon; that is, points which lie on the curve are stored in the computer memory and the curve between the points is interpolated linearly. Obviously, the standard curve can also be stored in a transformed form (for example, in a linearly transformed form). In this case, the transformation must be taken into consideration in the subsequent calculations.

It is moreover essential for the invention that a point on the standard curve in the vicinity of the point of inflection between the convexly and concavely curved sections be defined and stored in memory. This point is referred to as the "standard supporting point" and is labeled $R_{sb}$, $C_{sb}$ in FIG. 2.

The concept "in the vicinity of" is to be understood herein as being analogous to the concept "essentially" or "substantially" in the preceding third paragraph above; that is, the concentration value of the standard supporting point may not differ to such an extent from the concentration value of the point of inflection that the method for calculating the concentration from the measured values, as a whole, leads to unsatisfactory results. How large this deviation may be, in a particular case, can easily be determined for the particular case on the basis of the inventive teachings set forth herein. Quantitatively, it can be stated that the concentration value of the standard supporting point should deviate by not more than 20%, and preferably by not more than 10%, from the concentration value of the point of inflection.

Further, standard supporting points are in the vicinity of the ends of the concentration range that is to be determined. What is crucial here is the range of concentration values actually used under practical conditions and not the value range, which may possibly go beyond this first range and is technically possible, but is not used in practice by the particular analytical system. The concept "in the vicinity of" is to be understood similarly here in the same sense as in the preceding paragraph.

It is a further essential characteristic of the present invention that the batch-specific evaluation curves not be transmitted to the instrument in the form of a binary coded mathematical function which assigns a concentration value to each value of the diffuse reflectance, but that only a limited number of discrete value pairs, $R_{ia}$, $C_{ia}$; $R_{ib}$, $C_{ib}$, $R_{ic}$, $C_{ic}$..., from a finite number of permanently programmed calculation supporting points be transmitted. The calculation supporting points are therefore fixed in advance, independently of the evaluation curve and stored in the memory of the evaluating instrument. There is thus a set of calculation supporting points in the vicinity of each standard supporting point on the standard curve. Normally, an equal number of calculation supporting points is defined in the vicinity of each standard supporting point; that is, each set has the same number of points. For curves of the type shown in FIG. 2, with a standard supporting point in the vicinity of the single point of inflection and two further standard supporting points in the vicinity of the ends of the concentration range that is to be determined-that is, three standard supporting points altogether-three equally large sets of calculation supporting points are thus defined. Each of these sets may advantageously contain 16 different calculation supporting points (that is, the value pairs $R_{ia}$, $C_{ia}$, $R_{ib}$, $C_{ib}$, $R_{ic}$, $C_{ic}$ with $i=1 \ldots 16$, which define these calculation supporting points). These value pairs, stored in the instrument, are then selected in the manner described in connection with FIG. 1, for example with the aid of keys 26, 28, 30, to match the respective test strip batch. Each of the 16 alphanumeric characters, selectable with the keys 26, 28, 30, corresponds to a value pair. For example, the first character serves to select one of the 16 calculation supporting points $R_{ia}$, $C_{ia}$, the second character to select one of the 16 calculation supporting points $R_{ib}$, $C_{ib}$, and the third character to select one of the 16 calculation supporting points $R_{ic}$, $C_{ic}$. For each batch of test carriers, the user of the evaluating instrument receives instructions, for example in the form of an imprint on the packaging, with respect to the character sequence he or she should choose for selecting the calculation supporting points. By keying in this sequence of characters, one value pair is selected for each set of calculation supporting points.

The evaluating method according to the present invention is particularly advantageous if the number of bits of information, which must be set and transmitted for selecting the value pairs, is kept small. For this reason, the number of set of calculation supporting points, which are assigned to the standard supporting points on the standard curve, is limited to at most ten and preferably to at most five. For each test carrier batch, therefore, only a few value pairs of calculation supporting points are transmitted to the processor. The number of calculation supporting points per set is preferably at most 256.

As mentioned, the sets of calculation supporting points lie in the vicinity of the standard supporting points. The more precise position arises out of the iteration method described further below and can easily be implemented by those skilled in the art on the basis of the inventive teachings set forth.

Preferably, the calculation supporting points lie on a line which intersects the standard curve at an obtuse angle. Three such lines a, b and c have been drawn in FIG. 2. They are assigned to the standard supporting points $R_{sa}$, $C_{sa}$; $R_{sb}$, $C_{sb}$ and $R_{sc}$, $C_{sc}$. In the preferred embodiment shown, they intersect the standard curve at these points. Preferably, they are approximately straight lines as shown.

Figure 3:
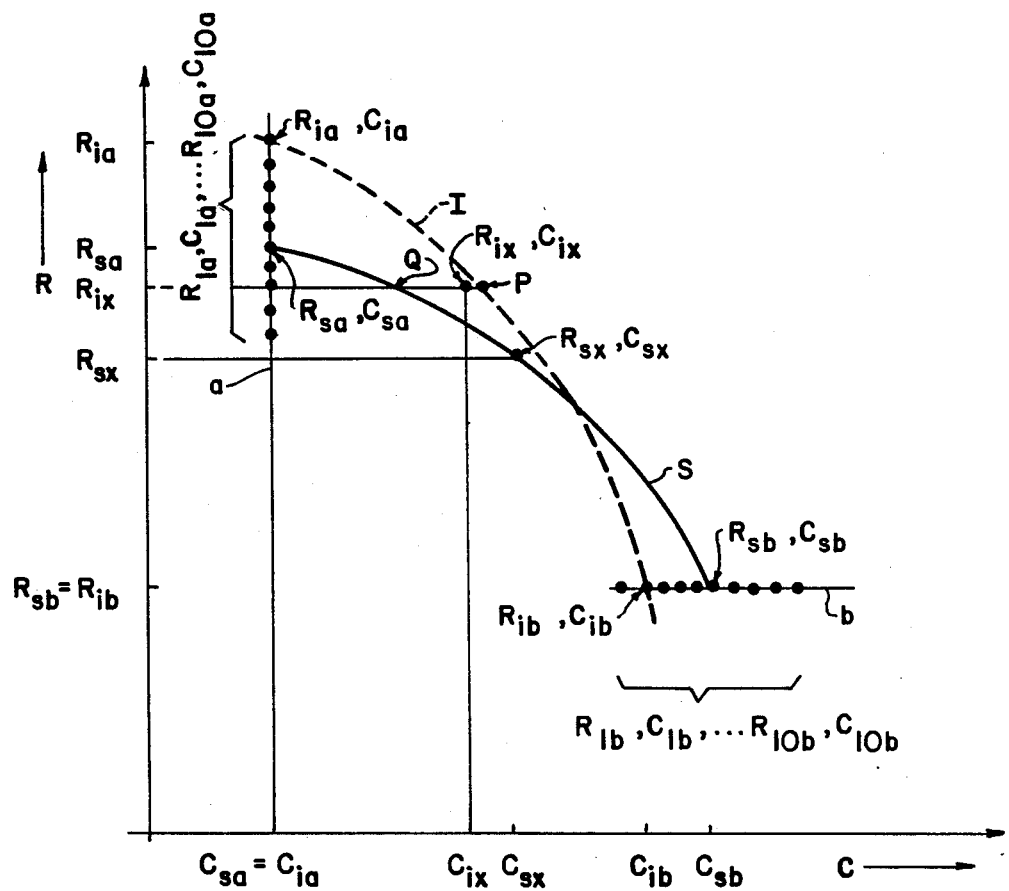
FIG. 3 is a section of a batch-specific evaluation curve and a standard evaluation curve in which the position of the calculation supporting point value pairs is altered relative to that of FIG. 2.

FIG. 3 shows only a portion of a standard curve S and an evaluation curve I and in particular, the portion lying between the two standard supporting points $R_{sa}$, $C_{sa}$; $R_{sb}$, $C_{sb}$ and two calculation supporting points $R_{ia}$, $C_{ia}$; $R_{ib}$, $C_{ib}$. For the simple embodiment of the invention shown here, the calculation supporting points in each case lie on straight lines which run parallel to a coordinate of the coordinate system. In the figure, ten calculation supporting points, assigned to the standard supporting points $R_{sa}$, $C_{sa}$ and $R_{sb}$ and $C_{sb}$ have been drawn. The calculation supporting points $R_{1a}$ and $C_{1a}$; ...; $R_{10a}$, $C_{10a}$, assigned to the standard supporting point $R_{sa}$, $C_{sa}$, lie on the straight line which is parallel to the ordinate of the coordinate system. Consequently, all of these calculation supporting points have the same concentration value as the corresponding standard supporting point ($C_{1a} = C_{2a} = \ldots = C_{10a} = C_{sa}$). This simplifies storage in the evaluating instrument because only the R value must be stored separately for each calculation point and the standard supporting point, whereas the C value, which is the same for all calculation supporting points and the standard supporting point, is stored only once. The corresponding situation applies also for the calculation supporting points $R_{1b}$, $C_{1b}$; ...; $R_{10b}$, $C_{10b}$, which lie on the straight line b that runs parallel to the abscissa. Here, the R value for all calculation supporting points is the same and is identical with the R value of the associated standard supporting point $R_{sb}$.

The method of calculating a concentration value $C_{ix}$ from the measured value of the diffuse reflection $R_{ix}$ will now be explained with further reference to FIG. 3.

For example, a diffuse reflectance having the value $R_{ix}$ is measured. The true evaluation curve of the test carrier used is shown as a broken line in FIG. 3 and labelled I. The horizontal line, defined by the measured value $R_{ix}$, intersects the curve I at point P. The concentration value, assigned to this point P, is thus the true concentration value which is to be determined. This concentration can be determined with complete accuracy only if the entire curve I for each batch is stored in the evaluating instrument. In principle, this is not possible since the evaluation curves of analytical test carriers cannot be represented exactly even by very complicated functions of higher order. Approximation methods are therefore used to represent the calibration curves. In particular, a concentration value $C_{ix}$ is assigned to each measured value $R_{ix}$, which value $C_{ix}$ corresponds with as good an approximation as possible at the point on the true evaluation curve at the value $R_{ix}$. In fact, this is possible by representing the respective evaluation curve of the test carrier batch in the form of a function of higher order, in the manner already discussed above, and transmitting the parameters of this function to the evaluating instrument. This, however, requires a substantial effort especially with respect to the evaluating instrument as was also explained above.

For simple evaluating instruments, therefore, a single, average, calibration curve is usually used for all test carrier batches. Assuming in FIG. 3 that the standard curve S, drawn there, is such an average evaluation curve, it can be seen that the horizontal line, corresponding to the measured value $R_{ix}$, intersects this curve at point Q. It can be seen at once that the concentration value, which corresponds to this point Q, deviates substantially from the true concentration value. Such a rough approximation is therefore completely unsatisfactory.

With very little effort, the present invention achieves a much better approximation of the true calibration curve owing to the fact that a standard measured value $R_{sx}$ on the standard curve S is initially calculated from the measured value $R_{ix}$, and then the desired concentration value $C_{ix}$ is calculated from the concentration value $C_{sx}$ corresponding to the standard measured value $R_{sx}$. The first step of the calculation uses, on the one hand, the distance between the two R values of the calculation supporting points closest to the measured value $R_{ix}$ (for example, $R_{ia}$-$R_{ib}$) and, on the other, the distance between the two R values of the standard supporting points (for example, $R_{sa}$-$R_{sb}$), to which these calculation supporting points are assigned. In this connection, the invention is based essentially on the discovery that, with appropriate choice of the calculation supporting points and the standard supporting points as well as a standard curve, similar to the evaluation curves in the sense discussed above, the relative change in a diffuse reflection value as compared to the adjacent calculation supporting point values proceeds with a surprisingly good approximation to the corresponding change along the standard curve in comparison to the standard supporting points.

This concept will now be explained in greater detail with the aid of FIG. 3. (This especially preferred linear approximation, which will now be described, is not, however, the only possible approximation method that may be used.) The algebraic sign convention of the calculation example cited is selected so that positive diffuse reflection values and concentration values result in the section of the curve shown. The algebraic signs can be changed appropriately for curve sections of a different nature.

To calculate the standard measured value $R_{sx}$ on the standard curve, the ratio $\alpha$ of the distance between the measured value $R_{ix}$ and the adjacent calculation supporting point $R_{ia}$ and $R_{ib}$ is initially formed. This ratio is multiplied by the distance between the standard supporting points $R_{sa}$ and $R_{sb}$, and the relative diffuse reflection decrease compared to the standard supporting point $R_{sa}$, so obtained, is subtracted from $R_{sa}$. The result is the standard measured value $R_{sx}$, which represents the value on the standard curve corresponding, in the sense of the present invention, to the measured diffuse reflectance $R_{ix}$.

$$R_{sx} = R_{sa} - \alpha(R_{sa} - R_{sb}); \alpha = \frac{R_{ia} - R_{ix}}{R_{ia} - R_{ib}}$$

This value $R_{sx}$ corresponds to a concentration value $C_{sx}$ on the standard curve S. This value is now converted by an appropriate approximation method, taking into consideration the distance between the concentration values $C_{ia}$, $C_{ib}$ of the adjacent calculation supporting points, on the one hand, and the distance between the concentration values of the adjacent standard supporting points $C_{sa}$, $C_{sb}$, on the other. In a linear approximation, the ratio of the distance between the value $C_{sx}$ and the adjacent standard concentration value $C_{sa}$ to the distance between the standard concentration values $C_{sa}$ and $C_{sb}$ is first formed. This ratio $\beta$ is then multiplied by the distance between the two concentration values of the calculation supporting points $C_{ib}$ and $C_{ia}$, and the result is added to the concentration value $C_{ia}$ of the adjacent calculation supporting point.

$$C_{ix} = \beta(C_{ib} - C_{ia}) + C_{ia}; \beta = \frac{C_{sx} - C_{sa}}{C_{sb} - C_{sa}}$$

The concentration value $C_{ix}$ is thus obtained. This concentration does not correspond exactly to the concentration value to be measured, but it is a very good approximation. This is illustrated in FIG. 3 by the fact that the point $C_{ix}$, $R_{ix}$ deviates slightly from the point P lying on the true evaluation curve I.

As mentioned, instead of the linear approximation described in detail, it is also possible to use a different approximating method in which the relationship of the distances mentioned between the calculation supporting points, on the one hand, and the standard supporting points, on the other, is taken into consideration. In special cases, a logarithmic or a quadratic approximation may be advisable. The linear approximation described is, however, particularly simple nd leads to very satisfactory, practical results.

The quality of the approximation in the method according to the invention depends essentially on the choice of the standard curve, the standard supporting points and the calculation supporting points. To optimize this method, an iteration procedure is recommended, which proceeds generally as follows.

A large number of test carrier batches is first of all prepared and the corresponding evaluation curves are accurately measured. A first standard curve is then placed so that it runs approximately through the middle of the evaluation curves. Thereupon, the standard supporting points are placed precisely at the points of inflection of the standard curve and at the ends of the measuring range. Straight or only slightly curved curves, running at an obtuse angle to the course or direction of the standard curve into the respective standard supporting point, are placed through the standard supporting points. For the sake of simplicity, straight lines, which run parallel to the axis of the coordinate system, should preferably be tried first. Calculation supporting points, which are equally spaced, are defined on these. The spacing and the distribution of the calculation supporting points on either side of the standard supporting point are then selected so that the outermost calculation supporting points still lie outside of the outermost evaluation curves of the test carrier batches investigated.

For each batch of test carriers, those calculation supporting points which lie as close as possible to the course of the curve are now selected from each set of calculation supporting points. With the help of these calculation supporting points and the inventive method, the approximate course of the evaluation curve is calculated, plotted graphically and compared with the respective actual evaluation curve. If all the previously measured calibration curves are portrayed correctly with the desired quality of approximation, the procedure is finished. In the usual case, however, at least some evaluation curves in at least some regions are not reproduced with the required quality. In such cases, the course of the standard curve and/or the selection of standard supporting points and of calculation supporting points are changed and a new sample run is carried out to check whether the necessary degree of accuracy is now reached. This procedure appears to be laborious, but can be carried out routinely and relatively rapidly with modern data processing equipment. What is crucial is that, on the basis of the fundamental teachings of the present invention, evaluation curves even of very complicated structure can be calculated with extremely little effort on the part of the evaluating instrument and with very high accuracy. It is, therefore, possible in the final analysis to take into consideration batch-specific deviations between test carriers in a relatively simply constructed and inexpensive instrument which at the same time is particularly easy to operate.

The invention can also advantageously be used for evaluating instruments with which several different types of test carriers are to be measured, thereby enabling the determination of several different parameters. In this case, the standard curve, the standard supporting points and the calculation supporting points are stored separately for each type of test carrier. Depending upon the course of the curves, it is, however, also possible that the same calculation supporting points or standard supporting points and, under some circumstances, also parts of the course of the standard curves can be used jointly for several test carrier types. By these means, less memory capacity is required. Obviously, for each test carrier batch of a particular test carrier type, the respectively assigned combination of calculation supporting points must be selected separately. If, for example, three sets of calculation supporting points are available for each type of test carrier, the selection can be made advantageously by a sequence of four alphanumeric characters. The first character may select the test carrier type. The other three characters may then select the calculation supporting points from the finite number of calculation supporting points stored for the respective type of test carrier.

Figure 4:
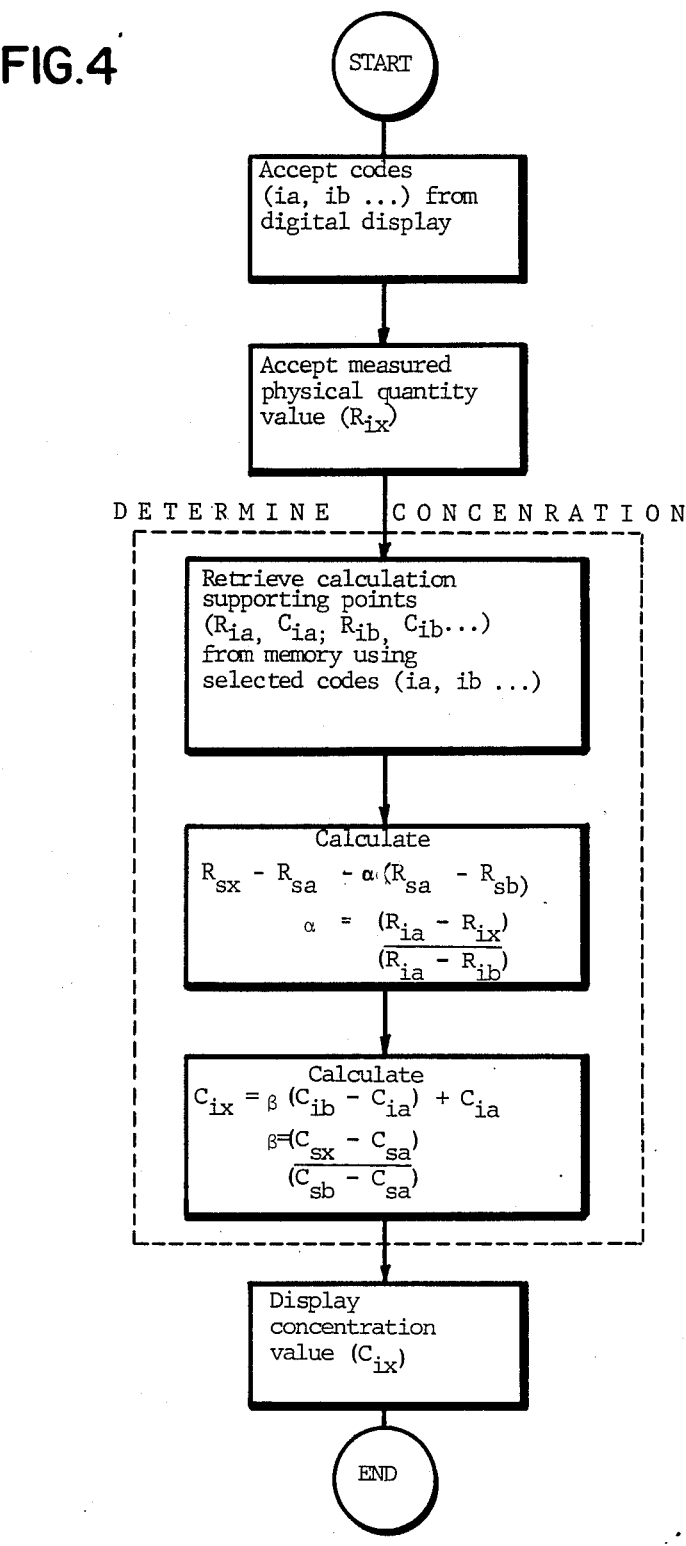
FIG. 4 is a flow diagram showing the sequence of steps carried out by the program run by the microcomputer contained in the evaluating instrument of FIG. 1.

FIG. 4 is a flow-chart of the program for the computer 20 in the evaluating instrument of FIG. 1. As may be seen, the program repeatedly checks the codes entered into the display device 24 by the keys 26, 28 and 30 before accepting the raw input data from the light detector 18. Thereafter, the concentration of the subject constituent of a body fluid is determined by the calculation method described above and this concentration is displayed on the display device 24.

Figure 5:
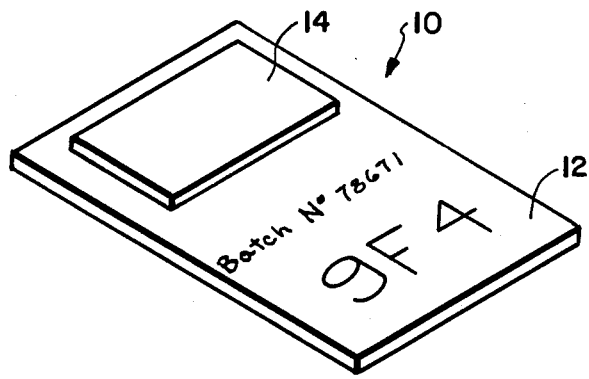
FIG. 5 is a perspective view of a test carrier on which are imprinted visible indicia (alphanumeric characters) according to the present invention.

FIG. 5 shows how the visible indicia, indicative of the calculation supporting points, may be imprinted on a test carrier 10. In this case, three alphanumeric characters "9 F 4" representing the selections of calculation supporting points from three respective sets of 16, are imprinted on the test carrier base 12. All of the test carriers manufactured in a single batch have common indicia.

Figure 6:
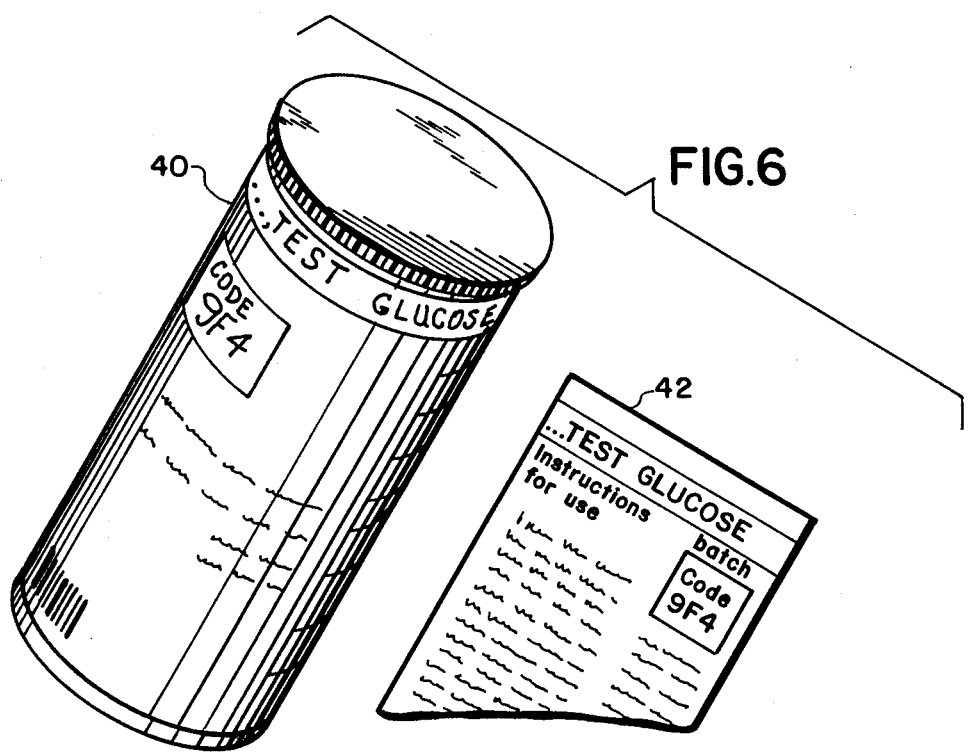
FIG. 6 is a perspective and cutaway view of a package of test carriers, all manufactured in a single batch, on which package is imprinted visible indicia (alphanumeric characters) according to the present invention.

FIG. 6 illustrates a preferred embodiment of the invention whereby the visible indicia are printed on a test carrier package 40 and/or a separate, removable record sheet 42 wrapped together with the test carriers manufactured in a single batch. This embodiment avoids the necessity of printing alphanumeric characters on the test carriers after they have been manufactured and tested to establish their evaluation curve.

While there have been described what are at present considered to be the preferred embodiments of this invention, it will be apparent to those skilled in the art that various changes and modifications may be made therein without departing from the invention. It is, therefore, intended to include all such changes and modifications as fall within the true spirit and scope of the invention.

I claim:

1. In a plurality of test carriers for use in a system for analyzing a constituent of a body fluid which is present in said fluid in a given concentration (C), said test carriers having been manufactured in batches, each of said test carriers comprising a base and a test field arranged on said base and impregnated with at least one reagent which reacts with said constituent when said body fluid is applied thereto to produce a measurable physical quantity (R) is dependence upon said concentration of said constituent in said body fluid, said dependence between said physical quantity and said concentration being different from manufactured batch to manufactured batch of the test carriers, but substantially following a standard, predictable, non-linear curve having two ends and at least one point of inflection, each of said ends and said at least one point of inflection defining a region immediately surrounding it; the improvement comprising:

a plurality of visible indicia disposed on each of said test carriers and representing calculation supporting points for said curve in the region of at least one of said ends and said at least one point of inflection thereof, each calculation supporting point being indicative of said dependence between said measurable physical quantity and said concentration in the respective region for the respective test carrier.

2. The improvement defined in claim 1, wherein said visible indicia are printed on said test carrier base.

3. In a system for analyzing a constituent of a body fluid which is present in said fluid in a given concentration (C), said system comprising (1) a plurality of test carriers having a base and a test field arranged on said base and impregnated with at least one reagent which reacts with said constituent when said body fluid is applied thereto to produce a measurable physical quantity (R) in dependence upon said concentration of said constituent in said body fluid, and (2) evaluating apparatus having a digital processor and a memory for determining said concentration from said physical quantity, said dependence between said physical quantity and said concentration being different from manufactured batch to manufactured batch of said test carriers, but substantially following a standard, predictable, non-linear curve having two ends and at least one point of inflection, each of said ends and said at least one point of inflection defining a region immediately surrounding it; the improvement comprising:
- a plurality of visible indicia disposed on each of said test carriers and representing calculation supporting points for said curve in the region of at least one of said ends and said at least one point of inflection thereof;
- each calculation supporting point being indicative of said dependence between said physical quantity and said concentration in the respective region for the respective test carrier;
- said evaluating apparatus comprising means for manually entering said visible indicia into said memory.

4. In a plurality of test carriers for use in a system for analyzing a constituent of a body fluid which is present in said fluid in a given concentration (C), said test carriers having been manufactured in batches, each of said test carriers comprising a base and a test field arranged on said base and impregnated with at least one reagent which reacts with said constituent when said body fluid is applied thereto to produce a measurable physical quantity (R) in dependence upon said concentration of said constituent in said body fluid, said dependence between said physical quantity and said concentration being different from manufactured batch to manufactured batch of the test carriers, but substantially following a standard, predictable, non-linear curve having two ends and at least one point of inflection therebetween, each of said ends and said at least one point of inflection defining a region immediately surrounding it; wherein a plurality of said test carriers which are manufactured together in a single batch are enclosed together in a common package; the improvement comprising:
- a plurality of visible indicia disposed on said package and representing calculation supporting points for said curve in the region of at least one of said ends and said at least one point of inflection thereof,
- each calculation supporting point being indicative of said dependence between said measurable physical quantity and said concentration in the respective region for the respective test carrier.

5. In a plurality of test carriers for use in a system for analyzing a constituent of a body fluid which is present in said fluid in a given concentration (C), said test carriers having been manufactured in batches, each of said test carriers comprising a base and a test field arranged on said base and impregnated with at least one reagent which reacts with said constituent when said body fluid is applied thereto to produce a measurable physical quantity in dependence upon said concentration of said constituent in said body fluid, said dependence between said physical quantity (R) and said concentration being different from manufactured batch to manufactured batch of the test carriers, but substantially following a standard, predictable, non-linear curve having two ends and at least one point of inflection therebetween, each of said ends and said at least one point of inflection defining a region immediately surrounding it; wherein a plurality of said test carriers which are manufactured together in a single batch are enclosed together in a common package, together with a separate, removable record medium wrapped with said test carriers in said common package; the improvement comprising:
- a plurality of visible indicia disposed on said separate record medium and representing calculation supporting points for said curve in the region of at least one of said ends and said at lest one point of inflection thereof;
- each calculation supporting point being indicative of said dependence between said measurable physical quantity and said concentration in the respective region for the respective test carrier.

6. The improvement defined in claim 1, 4 or 5, wherein each of said visible indicia identifies a particular calculation supporting point from among sets of points each set consisting of a finite number of prescribed calculation supporting points;
- each calculation supporting point comprising an associated coordinate value pair of said measurable physical quantity (R) and its associated body fluid constituent concentration (C) in an R-C coordinate plane;
- each set of calculation supporting points being located, respectively, in one of said regions of said ends and said at least one point of inflection of said curve on said R-C plane.

7. The improvement defined in claim 6, wherein said prescribed calculation supporting points in each set have different distances from the dependence between said physical quantity and said concentration for the respective test carrier, and wherein said calculation supporting points identified by said indicia are those points within said sets which are at least next to the closest to the dependence between said physical quantity and said concentration in the respective test carrier.

8. The improvement defined in claim 1, 4 or 5, wherein said visible indicia are alphanumeric characters.

9. The improvement defined in claim 8, wherein said visible indicia comprise a maximum of ten alphanumeric characters.

10. The improvement defined in claim 9, wherein said visible indicia comprise a maximum of five alphanumeric characters.

11. The improvement defined in claim 10, wherein said visible indicia comprise three alphanumeric characters.

12. The improvement defined in claim 8, wherein each visible indicium comprises one of a maximum of sixteen alphanumeric characters.

13. In a system for analyzing a constituent of a body fluid which is present in said fluid in a given concentration (C), said system comprising (1) a plurality of test carriers having a base and a test field arranged on said base and impregnated with at least one reagent which reacts with said constituent when said body fluid is applied thereto to produce a measurable physical quantity (R) in dependence upon said concentration of said constituent in said body fluid, and (2) apparatus having a digital processor and a memory for determining said concentration from said physical quantity, said dependence between said physical quantity and said concentration being different from manufactured batch to manufactured batch of said test carriers, but substantially following a standard, predictable, non-linear curve having two ends and at least one point of inflection therebetween, each of said ends and said at least one point of inflection defining a region immediately surrounding it; wherein a plurality of said test carriers which are manufactured together in a single batch are enclosed together in a common package; the improvement comprising:

a plurality of visible indicia disposed on said package and representing calculation supporting points for said curve in the region of at least one of said ends and said at least one point of inflection thereof;

each calculation supporting point being indicative of said dependence between said physical quantity and said concentration in the respective region for the respective test carrier;

said evaluating apparatus comprising means for manually entering said indicia into said memory.

14. In a system for analyzing a constituent of a body fluid which is present in said fluid in a given concentration (C), said system comprising (1) a plurality of test carriers having a base and a test field arranged on said base and impregnated with at least one reagent which reacts with said constituent when said body fluid is applied thereto to produce a measurable physical quantity (R) in dependence upon said concentration of said constituent in said body fluid, and (2) apparatus having a digital processor and a memory for determining said concentration from said physical quantity, said dependence between said physical quantity and said concentration being different from manufactured batch to manufactured batch of said test carriers, but substantially following a standard, predictable, non-linear curve having two ends and at least one point of inflection therebetween, each of said ends and said at least one point of inflection defining a region immediately surrounding it; wherein a plurality of said test carriers which are manufactured together in a single batch are enclosed together in a common package, together with a separate, removable record medium wrapped with said test carriers in said common package; the improvement comprising:

a plurality of visible indicia disposed on said separate record medium and representing calculation supporting points for said curve in the region of at least one of said ends and said at least one point of inflection thereof;

each calculation supporting point being indicative of said dependence between said physical quantity and said concentration in the respective region for the respective test carrier;

said evaluating apparatus comprising means for manually entering said indicia into said memory.

15. The improvement defined in claim 3, 13 or 14, wherein each of said visible indicia identifies a particular calculation supporting point from among sets of points, each set consisting of a finite number of prescribed calculation supporting points;

each calculation supporting point comprising an associated coordinate value pair of said measurable physical quantity (R) and its associated, body fluid constituent concentration (C) in an R-C coordinate plane;

each set of calculation supporting points being located, respectively, in one of said regions of said ends and said at least one point of inflection of said curve on said R-C plane.

16. The improvement defined in claim 15, wherein said prescribed calculation supporting points in each set having different distances on the R-C plane from the dependence between said physical quantity and said concentration for the respective test carrier, and wherein said calculation supporting points identified by said indicia are those points within said sets which are at least next to the closest to the dependence between said physical quantity and said concentration in the respective test carrier.

17. The system defined in claim 3, 13 or 14, wherein said indicia entry means includes a plurality of keys.

18. A method of analyzing a constituent of a body fluid which is present in said fluid in a given concentration (C), using a system comprising (1) a plurality of test carriers having a base and a test field arranged on said base and impregnated with at least one reagent which reacts with said constituent when said body fluid is applied thereto to produce a measurable physical quantity (R) in dependence upon said concentration of said constituent in said body fluid, (2) evaluating apparatus having a digital processor and a memory for determining said concentration from said physical quantity, said dependence between said physical quantity and said concentration being different from manufactured batch to manufactured batch of said test carriers, but substantially following a standard, predictable, non-linear curve having two ends and at least one point of inflection, each of said ends and said at least one point of inflection defining a region immediately surrounding it, and (3) a plurality of visible indicia disposed on each of said test carriers and representing calculation supporting points for said curve in the region of at least one of said ends and said at least one point of inflection thereof, each calculation supporting point being indicative of said dependence between said physical quantity and said concentration in the respective region for the respective test carrier, said evaluating apparatus comprising means for manually entering said visible indicia into said memory;

said method comprising the steps of:
(a) applying a body fluid to a test carrier;
(b) manually reading said visible indicia for a test carrier to be evaluated;
(c) manually entering said visible indicia into said evaluating apparatus by means of said entry means; and
(d) evaluating said test carrier by means of said evaluating apparatus to determine the concentration of said constituent of said body fluid applied to said test carrier.

19. A method for analyzing a constituent of a body fluid which is present in said fluid in a given concentration (c), said body fluid being applied to a test carrier and said method using apparatus for evaluating said test carrier;

said evaluating apparatus including means for measuring a physical quantity (R) on a test carrier as a measure of said concentration (C) of said body fluid constituent to be determined;

said test carrier being one of a plurality of test carriers which have been manufactured in batches;

the physical quantity (R) and the concentration (C) defining an evaluation curve of said test carrier, which is different, depending upon the manufacturing batch of said test carrier;

said method for determining the concentration (C) from the measured physical quantity (R) comprising the following steps:

(a) storing a standard evaluation curve in a memory, said standard curve being similar to that of the evaluation curves of the test carriers which are to be evaluated by said evaluating apparatus, said standard curve extending within a range of concentration values of said evaluation curves and having a substantially similar curvature in substantially the same sections of concentrations as said actual evaluation cures, thereby defining a plurality of standard concentration values ($C_{sx}$), said standard curve and said actual evaluation curves having two ends and at least one point of inflection therebetween; each of said ends and said at least one point of inflection defining a region immediately surrounding it and defining sections between said regions;

(b) defining a standard supporting point, comprising an R value and a C value ($R_{sa}$, $C_{sa}$; $R_{sb}$, $C_{sb}$; ...) on said standard curve in the region of each of said at least one point of inflection between a curved section and in the region of said range of values to be determined;

(c) storing a plurality of calculation supporting points, arranged in a plurality of sets, each particular set of calculation supporting points lying in said region of a standard supporting point and being assigned to such standard supporting points;

(d) selecting calculation supporting points, one from each set, from said sets of calculation supporting points;

(e) measuring the physical quantity (R) on a test carrier;

(f) converting the measured physical quantity (R) by an approximation procedure into a standard physical quantity ($R_{sx}$) on said standard evaluation curve, taking into consideration relative magnitudes of a distance between two R values ($R_{ia}$, $R_{ib}$) of the nearest calculation supporting point and a second distance between two R values ($R_{sa}$, $R_{sb}$) of the standard supporting points, to which the calculation supporting points are assigned; and (g) converting the standard concentration value ($C_{sx}$) on said standard evaluation curve, corresponding to said standard measured value ($R_{sx}$), into a final concentration value ($C_{ix}$) to be determined, taking into consideration the relative magnitude of the distance between the two concentration values ($C_{ia}$, $C_{ib}$) of a nearest calculation supporting point, and the distance between the two concentration values ($C_{sa}$, $C_{sb}$), to which the calculation supporting points are assigned.

20. The method of claim 19, wherein said standard measured value $R_{sx}$ is calculated by the linear approximation $$R_{sx} = R_{sa} - \alpha(R_{sa} - R_{sb}); \alpha = \frac{R_{ia} - R_{ix}}{R_{ia} - R_{ib}}$$

and said final concentration value is calculated by the linear approximation $$C_{ix} = \beta(C_{ib} - C_{ia}) + C_{ia}; \beta = \frac{C_{sx} - C_{sa}}{C_{sb} - C_{sa}}.$$

21. The method defined in claim 19, wherein each of said sets of calculation supporting points in the vicinity of a standard supporting point lie on an approximately straight line which intersects the standard curve at an obtuse angle.

22. The method defined in claim 19, wherein each of said set of calculation supporting points lie on a straight line which runs parallel to a coordinate of the R-C coordinate plane.

23. The method defined in claim 19, wherein step (c) includes the step of storing at least two, and at most five set of calculation supporting points.

24. A method of analyzing the presence of a constituent of a body fluid which is present in said fluid in a given concentration (c), using a system comprising (1) a plurality of test carriers having a base and a test field arranged on said base and impregnated with at least one reagent which reacts with said constituent when said body fluid is applied thereto to produce a measurable physical quantity (R) in dependence upon said concentration of said constituent in said body fluid, and (2) apparatus having a digital processor and a memory for determining said concentration from said physical quantity, said dependence between said physical quantity and said concentration being different from manufactured batch to manufactured batch of said test carriers, but substantially following a standard, predictable, non-linear curve having two ends and at least one point of inflection therebetween, each of said ends and said at least one point of inflection defining a region immediately surrounding it; wherein a plurality of said test carriers which are manufactured together in a single batch are enclosed together in a common package; wherein a plurality of visible indicia are disposed on said package and representing calculation supporting points for said curve in the region of at least one of said ends and said at least one point of inflection thereof; each calculation supporting point being indicative of said dependence between said physical quantity and said concentration in the respective region for the respective test carrier; and wherein said evaluating apparatus comprises means for manually entering said indicia into said memory;

said method comprising the steps of:

(a) applying a body fluid to a test carrier;

(b) manually reading said visible indicia for a test carrier to be evaluated;

(c) manually entering said visible indicia into said evaluating apparatus by means of said entry means; and (d) evaluating said test carrier by means of said evaluating apparatus to determine the concentration of said constituent of said body fluid applied to said test carrier.

25. A method of analyzing the presence of a constituent of a body fluid which is present in said fluid in a given concentration (c), using a system comprising (1) a plurality of test carriers having a base and a test field arranged on said base and impregnated with at least one reagent which reacts with said constituent when said body fluid is applied thereto to produce a measurable physical quantity (R) in dependence upon said concentration of said constituent in said body fluid, and (2)

apparatus having a digital processor and a memory for determining said concentration from said physical quantity, said dependence between said physical quantity and said concentration being difference from manufactured batch to manufactured batch of said test carriers, but substantially following a standard, predictable, non-linear curve having two ends and at least one point of inflection therebetween, each of said ends and said at least one point of inflection defining a region immediately surrounding it; wherein a plurality of said test carriers which are manufactured together in a single batch are enclosed together in a common package, together with a separate, removable record medium wrapped with said test carriers in said common package; wherein a plurality of visible indicia disposed on said separate record medium and representing calculation supporting points for said curve in the region of at least one of said ends and said at least one point of inflection thereof; each calculation supporting point being indicative of said dependence between said physical quantity and said concentration in the respective region for the respective test carrier; and wherein said evaluating apparatus comprising means for manually entering said indicia into said memory; said method comprising the steps of:

(a) applying a body fluid to a test carrier;
(b) manually reading said visible indicia for a test carrier to be evaluated;
(c) manually entering said visible indicia into said evaluating apparatus by means of said entry means; and
(d) evaluating said test carrier by means of said evaluating apparatus to determine the concentration of said constituent of said body fluid applied to said test carrier.

* * * * *